(12) United States Patent
Caizza et al.

(10) Patent No.: US 8,574,193 B2
(45) Date of Patent: Nov. 5, 2013

(54) RETRACTABLE SYRINGE WITH LOCKING PLUNGER

(75) Inventors: Richard Caizza, Vernon, NJ (US); Jay Bojan, Littleton, CO (US)

(73) Assignee: Midland Medical Devices Holdings, LLC., Midland, TX (US)

( * ) Notice: Subject to any disclaimer, the term of this patent is extended or adjusted under 35 U.S.C. 154(b) by 0 days.

(21) Appl. No.: 13/413,577

(22) Filed: Mar. 6, 2012

(65) Prior Publication Data

US 2012/0232483 A1 Sep. 13, 2012

Related U.S. Application Data

(60) Provisional application No. 61/449,998, filed on Mar. 7, 2011.

(51) Int. Cl.
*A61M 5/00* (2006.01)
(52) U.S. Cl.
USPC .......................................... 604/110
(58) Field of Classification Search
USPC .......................................... 604/110
See application file for complete search history.

(56) References Cited

U.S. PATENT DOCUMENTS

| 5,531,693 | A | 7/1996 | Vounatsos |
| 6,485,459 | B1 | 11/2002 | Surowitz |
| 8,034,025 | B1 * | 10/2011 | Chang ........................ 604/110 |
| 2006/0189935 | A1 * | 8/2006 | Janek et al. ................ 604/110 |
| 2011/0092902 | A1 * | 4/2011 | Kiehne ....................... 604/110 |

FOREIGN PATENT DOCUMENTS

| EP | 1106194 A1 | 6/2001 |
| KR | 10-0629274 B1 | 10/2006 |

OTHER PUBLICATIONS

International Search Report and Written Opinion—PCT/US2012/027925, (Sep. 28, 2012).

* cited by examiner

*Primary Examiner* — Jason Flick
(74) *Attorney, Agent, or Firm* — Robert C. Klinger

(57) ABSTRACT

A retractable needle syringe having a plunger rod configured to lock in place after retraction of the needle. The plunger rod distal end has a seal configured to advance past a retaining ledge after retraction of the needle, whereby the retaining ledge restricts or inhibits the plunger from proximal movement.

14 Claims, 6 Drawing Sheets

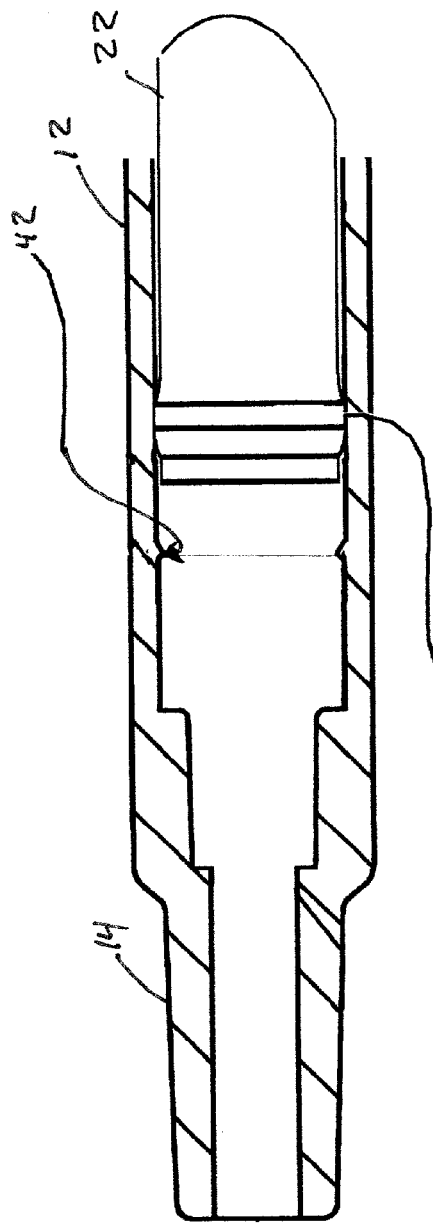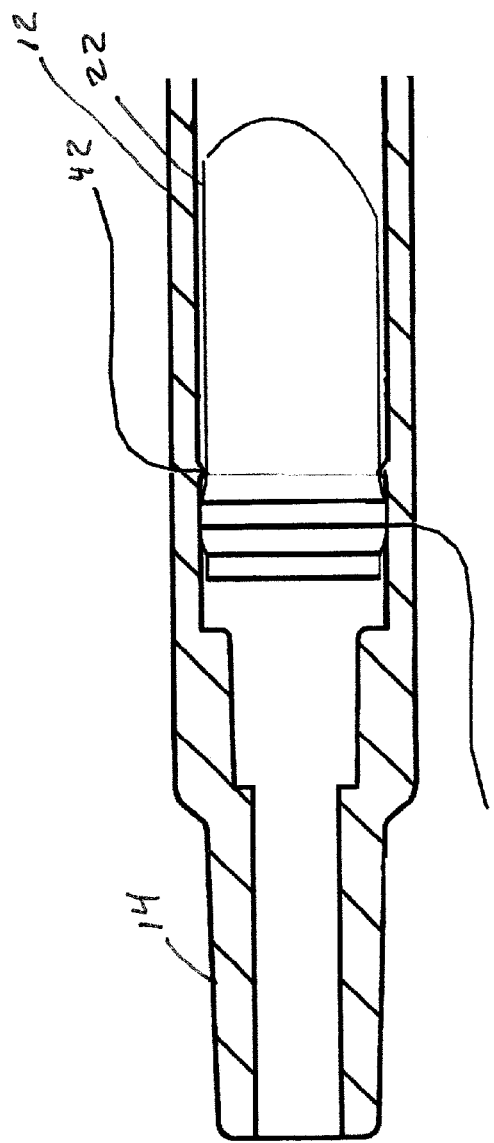

RETRACTABLE SYRINGE WITH LOCKING PLUNGER

CROSS REFERENCE TO RELATED APPLICATIONS

This application claims priority of U.S. Provisional Patent Application Ser. No. 61/449,998 entitled Retractable Syringe with Locking Plunger, filed Mar. 7, 2011, the teachings of which are incorporated herein.

BACKGROUND OF THE INVENTION

The present invention is directed to safety syringes, and particularly syringes with retractable needles configured to retract after use and prevent re-use and unintended sticking. Retractable syringes are known in the art, which typically include a needle configured to automatically retract into a syringe barrel after delivery of a medicant into a patient. In some designs, a needle stem including a separable or breakable retaining ring thereabout is installed through a barrel proximal end and secured in the barrel distal end. The needle stem may be fixedly secured or selectively secured to a needle. Conventional mechanisms that prevent or inhibit retracting the plunger after retraction of the needle into the syringe barrel have relative advantages and disadvantages, including complexity and cost.

There is desired an improved retractable syringe configured to restrict the plunger from being withdrawn from the syringe barrel after use and retraction of the needle assembly.

BRIEF DESCRIPTION OF THE FIGURES

FIG. 6 details the plunger with an integrated seal prior to engagement with the seal ring and retraction of the needle; and FIG. 7 shows the plunger seal ring advanced past the annular retaining ledge and locked in position after retraction of the needle.

SUMMARY OF THE INVENTION

The present invention achieves technical advantages as a retractable needle syringe having a plunger rod configured to lock in place after retraction of the needle. The plunger rod distal end has a seal configured to advance past a retaining ledge after retraction of the needle, whereby the retaining ledge restricts or inhibits the plunger from proximal movement.

DETAILED DESCRIPTION OF A PREFERRED EMBODIMENT

Figure 1:
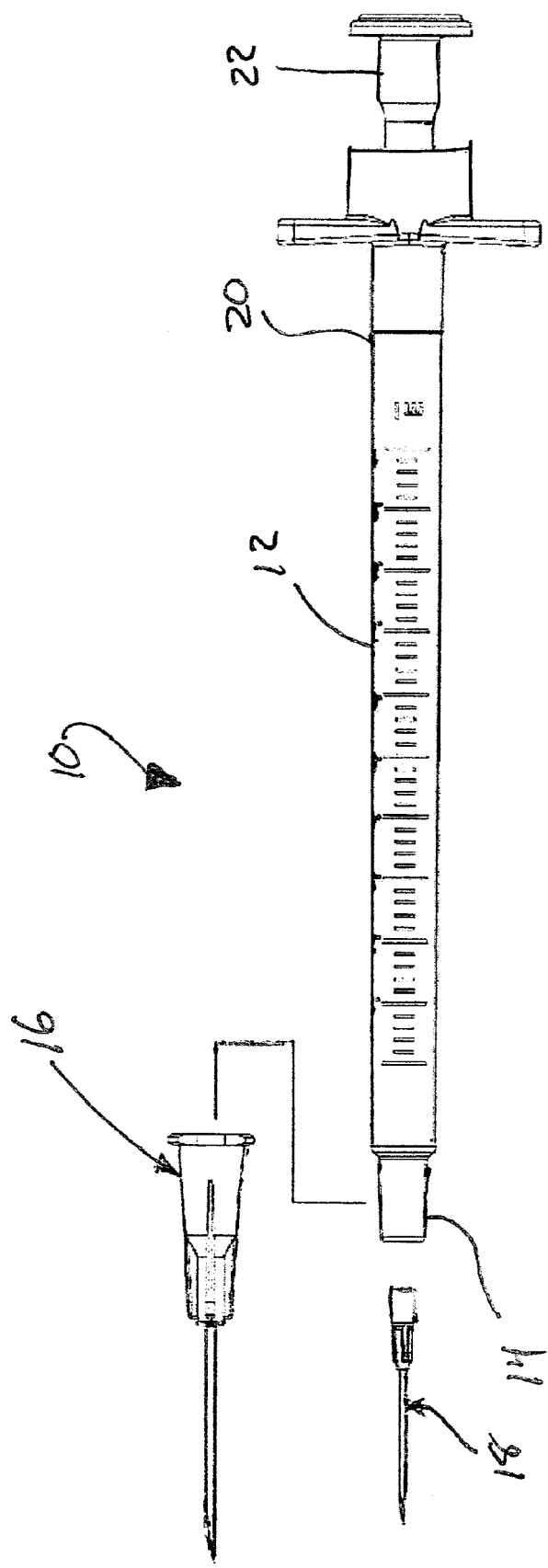
FIG. 1 shows an exploded view of a retractable syringe having a conical frustum tip, as well as an interchangeable needle and hub forming a needle assembly configured to extend through the conical frustum Tip.

Referring to FIG. 1 there is shown a retractable needle syringe 10 having a syringe barrel 12 with a distal end 14 configured as a conical frustum tip. The conical frustum tip 14 is configured to attach to female Luer compatible devices including a filling needle & Luer hub 16 as shown, collectively referred to as a luer filling needle, as well as delivery tubes and the like. The syringe 10 is also shown to include a selectively attachable, interchangeable needle assembly 18 including a needle and threaded needle hub, allowing needles of different sizes and lengths to be interchanged with the syringe 10. Needle assembly 18 has radially extending ribs and is configured to be threadably coupled to a threaded needle stem 24 within the distal end of the conical frustum tip 14, as shown in the FIG. 2 as will be described shortly. Syringe 10 also includes a syringe proximal end 20 and a plunger 22 slidable therein from the proximal end, the plunger 22 configured to both aspirate a fluids through the Luer filling needle/hub 16, and also dispense the medicant upon compression. The plunger 22 is also configured to aspirate a fluid through the needle assembly 18 if desired. The filling needle/hub 16 may be desired as it is a common inexpensive needle that can also speed up the drawing process, and also prevents the possible unintentional retraction of the needle assembly 18 during insertion into the medicant vial or during the handling of the syringe 10 when drawing the medicant. Moreover, the conical frustum tip 14 advantageously allows the syringe 10 to be conveniently prefilled with medicant at one place and capped, then transported to a patient with or without needle assembly 18 as desired. This design is a significant advantage for many healthcare providers involved in the processing and handling of syringes until ultimate delivery of the medicant to a patient.

Figure 2:
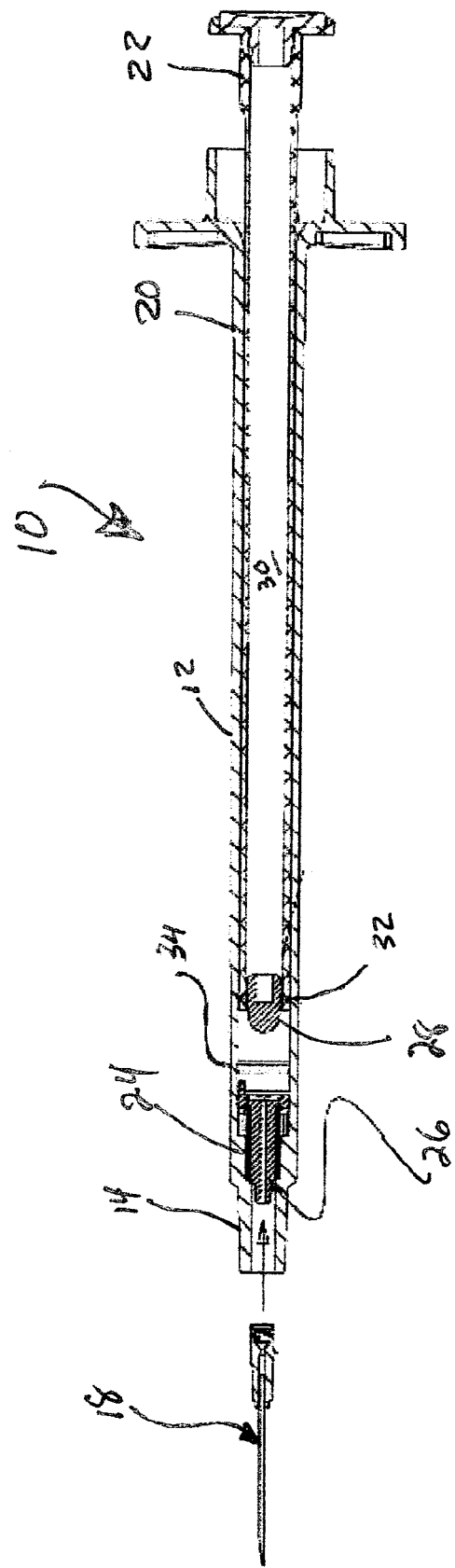
FIG. 2 shows a longitudinal cross sectional view of the syringe of FIG. 1 depicting a needle stem positioned in the syringe distal end and configured to receive the interchangeable needle assembly disposed through the conical frustum tip.

Referring to FIG. 2, there is shown a longitudinal cross sectional view of syringe 10 of FIG. 1, detailing the needle stem 24 having a threaded distal end 26 configured to receive the needle assembly 18. Notably, the needle stem 24 is positioned within the distal end of the conical frustum tip 14 and is advantageously protected from axial forces which could inadvertently being contacted and creating an unintended retraction of spring biased needle stem 24, such as when the needle assembly is secured to needle stem. Also shown is the plunger 22 having a plug 28 at a distal end thereof, which plug is in sealing arrangement with a cavity 30 of plunger 22 prior to retraction of needle assembly 18 therein, and which plug is dislodged into the cavity by the needle stem 24 that retracts with needle assembly 18 after an injection. The distal end of plunger 22 proximate the plug 28 has an integral seal 32 extending annularly thereabout. The interior surface of the syringe includes a plurality of annular detents 34 configured for positioning the seal 32 in a rested position, before the distal end of plunger 22 axially engages a protrusion 38 of an annular ring 36 coupled to the needle stem 24 by a breakable membrane, as more fully described in Applicant's U.S. Pat. No. 7,803,132 B1, the teaching of which are included herein by reference.

Figure 3:
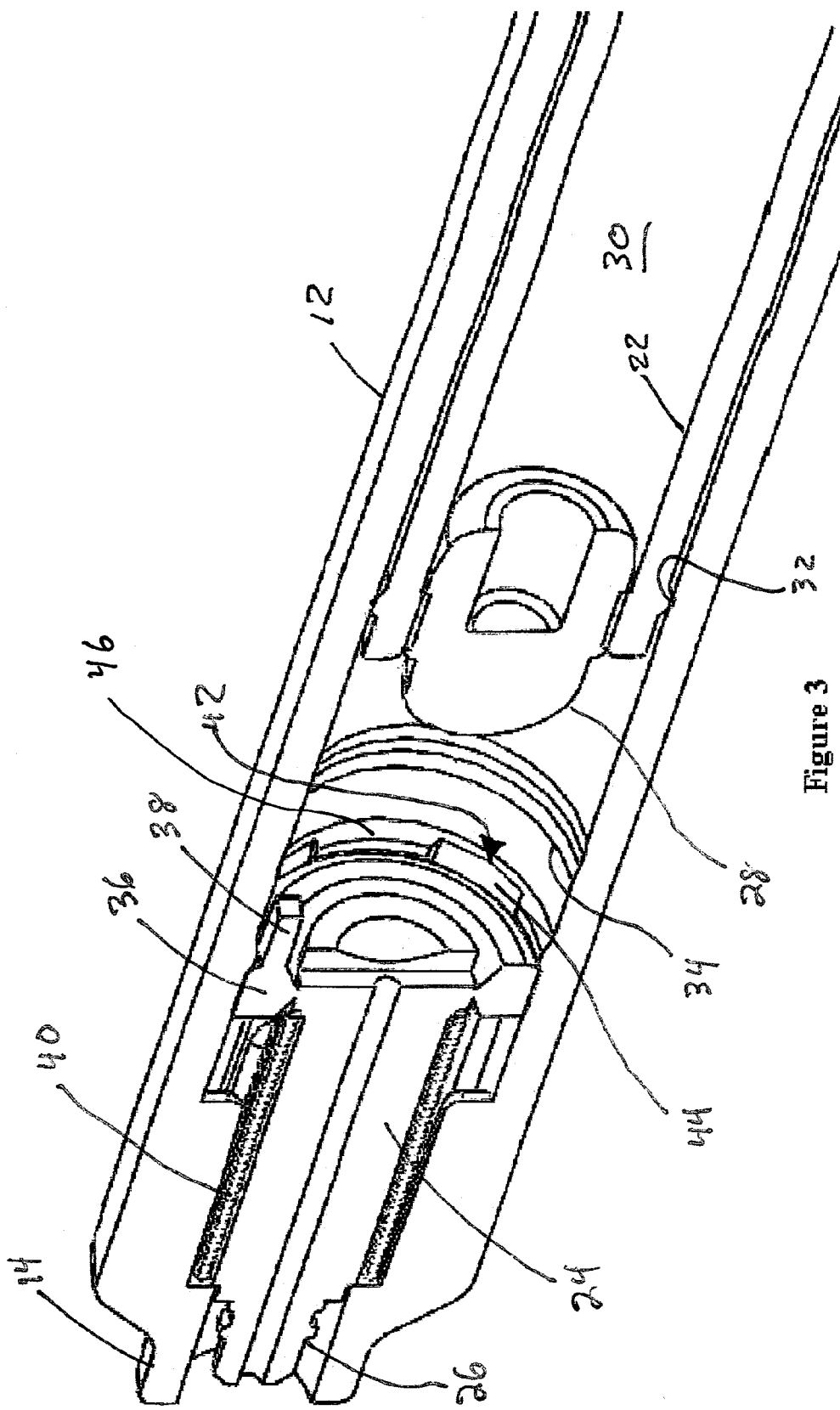
FIG. 3 shows an enlarged sectional view of the syringe distal end illustrating the needle stem having a threaded distal end configured to receive needles of various sizes through the conical frustum tip.

FIG. 3 depicts an enlarged cross sectional view of the needle stem 24, including the threaded needle distal end 26, positioned within the conical frustum tip 14, and coupled to the retaining ring 36 with protrusion 38 by the breakable membrane. Also shown is a spring 40 configured to retract the needle assembly 18 in response to the plunger 22 engaging the protrusion 38 after delivering the medicant to create a progressive separation of the retaining ring 36 from the needle stem 24 and the retraction of needle stem 24 into the plunger cavity 30. The annular detents 34 configured to seat position seal 32 are also shown.

This FIG. 3 also shows the interior surface of the barrel 12 including an annular retaining ledge generally shown at 42 configured to retain the needle stem 24 distally thereof such that the needle stem 24 is securely seated in the syringe barrel distal end, including during attachment of needle assembly 18, and until a complete retraction of the needle stem 24 and needle assembly 18 into cavity 30. Notably, the retaining ledge 42 is segmented, and is defined by segments of raised protrusions 44 extending from the interior barrel wall with notches or detents 46 defined between the protrusions 44 to provide several features. The segmented retaining ledge 42 enables reduced activation force required by the plunger to separate and break the retaining ring 36 from the needle stem 24, which provides an improved tactile feeling of the seal 32 and comfort of use. The segmented ledge 42 also makes it easier to install the needle stem 24 and retaining ring 36 in the barrel distal end, such that it snaps into place therepast with less axial force.

Figure 4:
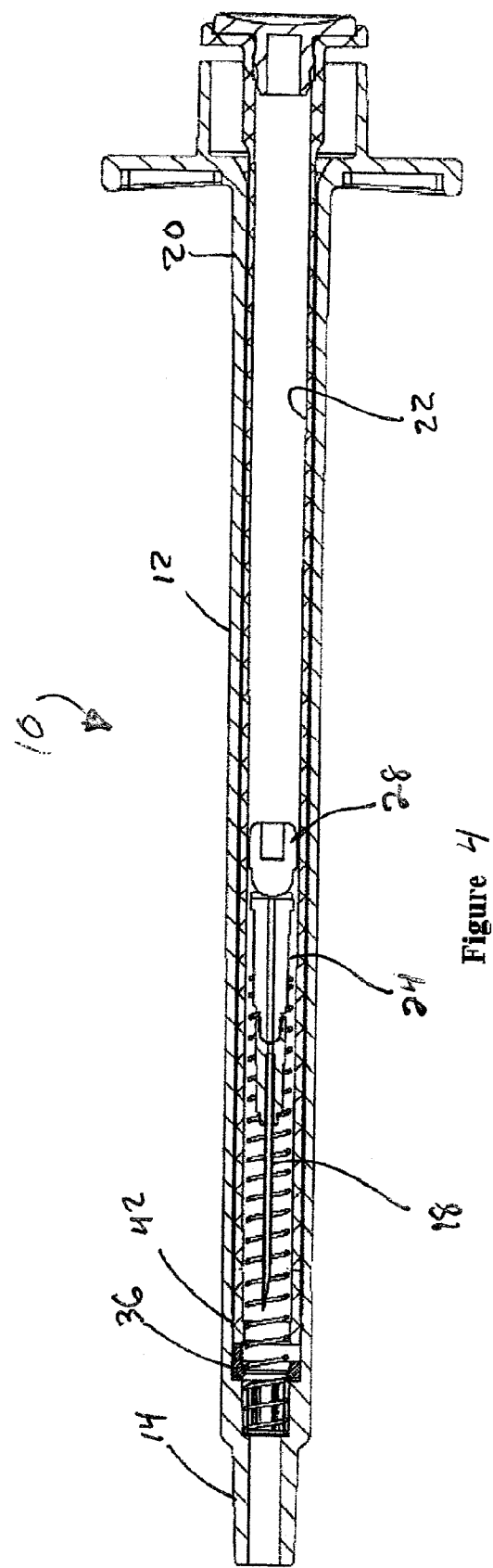
FIG. 4 shows a longitudinal cross sectional view of the syringe of FIG. 1 depicting the needle assembly after retraction into the syringe barrel.

FIG. 4 depicts the needle stem 24 and needle assembly 18 after retraction into the plunger cavity 30.

Figure 5:
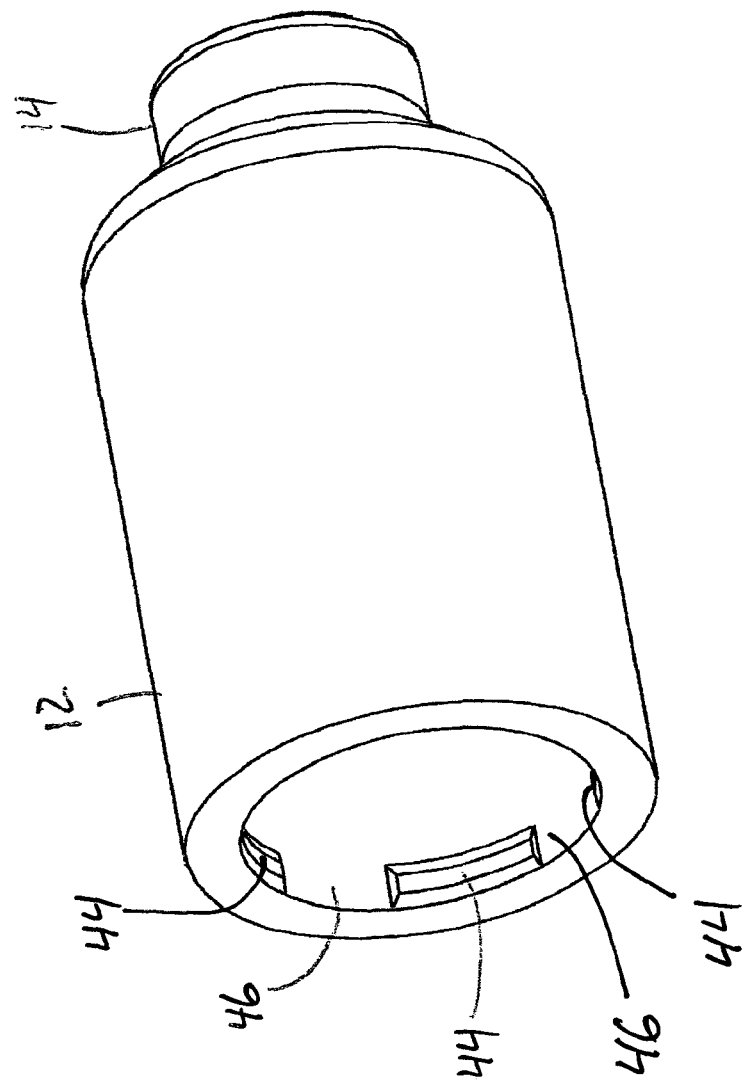
FIG. 5 shows a cross section of the syringe barrel just distal of the segmented retaining ledge shown in FIG. 3.

FIG. 5 depicts a cross section of the syringe barrel distal end taken proximate the segmented retaining ledge 42.

Turning now to FIG. 6, there is shown a plunger locking system configured to restrict withdrawing the plunger rod 22 from the syringe barrel after dispensing the medicant and the needle assembly 18 has been retracted into the plunger cavity. FIG. 6 depicts the plunger rod 22 before engagement with the retaining ring 36 (not shown), with the integrated seal 32 being disposed proximal of the segmented retaining ledge 42. According to this embodiment, the retaining ring does not need to be segmented to establish the advantageously locking mechanism. In the alternative, the engaging integrated seal could be configured to be some structure on the plunger tip in combination with a separable seal consistent with the black piston seal often found in syringes.

FIG. 7 depicts the plunger rod 22 after the retaining ring 36 (not shown) has been separated from needle assembly 18, whereby the plunger seal 32 is advanced past the retaining ledge 42 and locked into place. This arrangement helps secure the plunger rod 22 in place after use of the syringe and retraction of the needle assembly 18 into the plunger cavity 30. This configuration allows the plunger to be advanced further into the syringe barrel after use, restricting the plunger from being withdrawn or inadvertently withdrawn after use.

While the invention has been described in detail and with reference to a specific embodiment thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents.

We claim:

1. A syringe, comprising:
a barrel having a proximal end and a distal end, and an interior surface defining a cavity configured to hold a medicant;
a plunger having an annular seal disposed in the barrel and configured to advance toward the barrel distal end;
a needle stem disposed in the barrel distal end; a needle coupled to the needle stem and configured to deliver the medicant upon advancement of the plunger toward the barrel distal end, the needle stem and needle configured to retract into the barrel after delivery of the medicant; and
wherein the barrel interior surface comprises a retaining ledge at the barrel distal end, wherein the annular seal is configured to advance distal of the retaining ledge after retraction of the needle and needle stem, and wherein the retaining ledge is configured to secure the plunger in the barrel distal end, wherein the retaining ledge comprises a plurality of members extending inwardly from the barrel interior surface with a space defined between each of the members.

2. The syringe as specified in claim 1 wherein the retaining ledge is configured to engage the annular seal to restrict or inhibit proximal movement of the plunger after being advanced distal of the retaining ledge.

3. The syringe as specified in claim 2 wherein the annular seal is configured to be spaced past the retaining ledge after retraction of the needle and the needle stem into the barrel.

4. The syringe as specified in claim 1 wherein the retaining ledge extends annularly about the barrel cavity.

5. The syringe as specified in claim 1 wherein the members are uniformly spaced from one another.

6. The syringe as specified in claim 1 wherein the plunger has a tip consisting of one or more elements configured to engage with the retaining ledge to secure the plunger after retraction.

7. The syringe as specified in claim 1 wherein the needle stem includes a retaining ring disposed annularly thereabout, wherein the retaining ledge is configured to reduce an engagement force of the plunger necessary to separate the retaining ring from the needle stem.

8. The syringe as specified in claim 7 wherein the retaining ring is configured to be broken from the needle stem, wherein the retaining ledge is configured to reduce an engagement force of the plunger necessary to break the retaining ring from the needle stem.

9. The syringe as specified in claim 1 wherein the needle stem includes a retaining ring disposed annularly thereabout, wherein the retaining ledge is configured to reduce an axial force required to advance the retaining ring distally therepast.

10. The syringe as specified in claim 9 wherein the retaining ledge has rounded surfaces configured to engage the needle stem as it is advanced distally therepast during installation into the barrel distal end.

11. The syringe as specified in claim 1 wherein the needle stem and the needle are configured to automatically retract past the retaining ledge and within the barrel upon delivery of the medicant from the barrel.

12. The syringe as specified in claim 11 wherein the needle stem is spring biased toward the barrel proximal end.

13. The syringe as specified in claim 1 wherein the barrel has a space distal of the retaining ledge, wherein the needle stem is configured to snap distal of the segmented retaining ledge and seat in the space.

14. The syringe as specified in claim 1 wherein the needle is configured to be selectively coupled to the needle stem.

* * * * *